United States Patent [19]

Schoedel et al.

[11] Patent Number: 5,625,110
[45] Date of Patent: Apr. 29, 1997

[54] HYDRODEHALOGENATION CATALYST

[75] Inventors: Rainer Schoedel, Halle; Hans-Dieter Neubauer, Merseburg; Peter Birke, Langenbogen; Hans-Dieter Berrouschot, Langendorf; Hans-Georg Friese, Halle; Klaus Weber, Duerrenberg; Ulrich Neumann, Halle; Hannelore Grundmann, Leuna, all of Germany

[73] Assignee: Leuna-Katalysatoren GmbH, Leuna, Germany

[21] Appl. No.: 504,630

[22] Filed: Jul. 20, 1995

[30] Foreign Application Priority Data

Jul. 26, 1994 [DE] Germany ............ 44 26 389.9
Jul. 26, 1994 [DE] Germany ............ 44 26 390.2

[51] Int. Cl.$^6$ ........................................... C07C 1/00
[52] U.S. Cl. .................. 585/641; 585/733; 502/240; 502/262
[58] Field of Search ................ 502/240, 262; 585/733, 641; 208/262.1; 423/240 B, 241 S

[56] References Cited

U.S. PATENT DOCUMENTS

| 3,855,347 | 12/1974 | Oricchio ................. 260/683.9 |
| 4,152,291 | 5/1979 | Drake ........................ 252/416 |
| 4,749,817 | 6/1988 | George et al. ............ 570/204 |
| 5,004,859 | 4/1991 | Schmidt et al. ........... 585/741 |
| 5,177,268 | 1/1993 | Balko et al. ............... 568/726 |
| 5,292,975 | 3/1994 | Schrage et al. ........... 570/147 |

FOREIGN PATENT DOCUMENTS

| 44236A1 | 8/1991 | European Pat. Off. . |
| 0442236A1 | 8/1991 | European Pat. Off. . |
| 0570050A1 | 11/1993 | European Pat. Off. . |
| 1036830 | 8/1958 | Germany . |
| 294965 | 10/1971 | Germany . |
| 2164074 | 6/1973 | Germany . |
| 4200790A1 | 7/1993 | Germany . |
| 61442 | 8/1976 | Romania . |
| 267472 | 7/1990 | Russian Federation . |

*Primary Examiner*—Deborah Jones
*Assistant Examiner*—Amy M. Harding
*Attorney, Agent, or Firm*—Jordan and Hamburg

[57] ABSTRACT

A new hydrodehalogenation catalyst, as well as to its use for the hydrodechlorination of chlorinated hydrocarbons. The hydrodehalogenation catalyst, which converts halogenated hydrocarbons completely under mild conditions, has a considerably longer lifetime than do known catalysts and can be regenerated. In a method of hydrogenating dechlorination the catalyst works preferably under mild reaction conditions, with lifetimes of at least 2,500 hours and leads to reaction products, which can readily be used economically and thermally without further purification. The catalyst is a palladium aluminosilicate support catalyst, which is free of chlorinated compounds, has a palladium content of 0.5 to 8% by weight and a silica content of 1 to 50% by weight. The palladium concentration over the cross section of the support passes through a maximum in the region 50 to 250 µm below the outer surface of the support, the maximum palladium concentration is 1.5 to 7 times the average palladium concentration.

13 Claims, No Drawings

HYDRODEHALOGENATION CATALYST

BACKGROUND OF THE INVENTION

The invention relates to a new hydrodehalogenation catalyst and to its use for the hydrodechlorination of chlorinated hydrocarbons. The catalyst is suitable for hydrodehalogenation under mild reaction conditions, such as a temperature of 30° to 230° C. and pressures from atmospheric to 8 bar.

Chlorinated hydrocarbons are a by-product of numerous processes of the chemical industry. Because of the high toxicity of these compounds, it is necessary to eliminate them from halogenated organic waste. For this purpose, noncatalytic methods, such as the treatment with metallic sodium (DEGUSSA Method), the high temperature combustion, UV irradiation and adsorption methods, as well as catalytic methods have been used. The predominant catalytic methods are the heterogeneous catalytic methods, the hydrogenating dechlorination and the catalytic combustion.

The danger of forming dioxins and the combustion of valuable hydrocarbons are disadvantages of the catalytic combustion methods. For this reason, there has been more emphasis on methods for the hydrogenating disposal of chlorinated hydrocarbons.

One such method is the hydrogenating conversion of chlorobenzenes on nickel-containing catalysts, as described in the patents RO 61 442 and DD 294 965. However, the catalysts used here have the disadvantage that they cannot be reactivated.

The hydrogenating dechlorination of chlorinated hydrocarbons on rhodium support catalysts is described in DE 2 164 074. At a loading of approximately 0.1 v/vh at 180° C., atmospheric pressure and a molar ratio of dichloropropane to hydrogen of 1:3.5, it was possible to achieve complete conversion over a period of 400 hours. The high costs of rhodium are, however, a disadvantage of this catalyst system.

The use of a catalyst consisting of platinum, palladium, rhodium, ruthenium and/or mixtures of these on an iron and/or nickel basic alloy with a chromium content of at least 15% and coated with titanium dioxide is protected in the German patent 4 200 790. The lifetime of these catalysts was not given in this patent. Moreover, conversions are incomplete even at temperatures of 250° C.

The CS 267 472 patent discloses the catalytic hydrogenation of hexachlorobenzene to cyclohexane in the presence of palladium supported catalysts containing 0.1 to 5% by weight of palladium, carbon, silica or alumina being used as support. However, these catalysts preferably work only at temperatures from 220° to 280° C.

The U.S. Pat. No. 3,855,347 discloses a catalyst, which was produced by impregnating silica/alumina with a $H_2O$-$HCl$-$PdCl_2$ solution. This catalyst dehydrochlorinated 1,2-dichloropropane. However, the reaction was incomplete even at 320° C.

Moreover, the DE-AS 1 036 830 describes Pd-$Al_2O_3$-$SiO_2$ catalysts, which were prepared by suspending support gels in palladium nitrate solutions, for the hydrogenation of alkylated or arylated anthraquinones. However, this method of manufacture does not permit the distribution of the palladium to be adjusted selectively over the cross section of the catalyst castings.

The hydrogenation dechlorination of chloromethanes in the presence of a noble metal-containing supported catalyst with an alumina support, which preferably has a surface area of 5–90 $m^2/g$, up to 0.1% of silica and up to 2% of other metal oxides such as $TiO_2$, $Fe_2O_3$ and $Na_2O$, is described in the EP 570 050. With this method also, only partial conversion is achieved, as is evident from the examples given.

As has already been shown partly, all the catalysts mentioned have a series of disadvantages. For example, the use of some catalysts is restricted to only a certain group of chlorinated hydrocarbons, and/or the working temperature of the catalyst lies above 230° C. In particular, the lifetimes of the known catalysts are unsatisfactory, the longest one described being 400 hours.

SUMMARY OF THE INVENTION

It is therefore an object of the present invention to develop catalysts for the hydrogenating disposal of chlorinated aliphatic, cyclic and aromatic hydrocarbons, which preferably work at temperatures from 70° to 200° C., have lifetimes of at least 2,500 hours and can be regenerated, as well as to develop a method particularly for hydrogenating dechlorination, which operates preferably under mild reaction conditions, with catalyst lifetimes of more than 2,500 hours and leads to reaction products, which can readily be utilized as such or thermally.

Pursuant to the invention, this objective is accomplished by a chlorine-free palladium aluminosilicate catalyst with a palladium content of 0.5 to 8% by weight and a silica content of 1 to 50% by weight, the palladium concentration over the cross section of the support passing through a maximum in the region from 50 to 250 μm below the outer surface of the support and the palladium concentration in this region being about 1.5–7-fold the average palladium concentration in the catalyst. In a preferred variation of the catalyst, the palladium content is 2.2 to 6% by weight and the silica content 35 to 45% by weight.

The catalyst is prepared by impregnating support castings with chlorine-free palladium salt solutions corresponding to their absorption of water or from a supernatant solution. The ratio of solution volume to support volume should not exceed 2:1. Spheres with diameters of 1 to 3 mm or strands with diameters of 1.8 to 3 mm have proven to be appropriate as supports castings.

After the support is impregnated, the catalyst is dried and subsequently reduced at temperatures of 100° to 500° C. in a current of hydrogen. Before the reduction, the catalyst can also be calcined at temperatures of 350° to 450° C.

Surprisingly, it was found that the inventive catalyst has high activities and a long lifetime under mild reaction conditions.

The advantages of the inventive catalyst consist primarily of the preferably low operating temperature of less than 200° C., of the lifetimes of at least 2,500 hours and of the simple manner, in which it can be manufactured.

DETAILED DESCRIPTION OF THE INVENTION

This catalyst, which can be regenerated and is chlorine-free in the unused state, is used pursuant to the invention for the hydrogenating dechlorination of chlorinated hydrocarbons and/or of technical mixtures in which the chlorinated hydrocarbons are concentrated, in the gas phase, with hydrogen or hydrogen-containing gases, at temperatures of 30° to 350° C., at pressures of up to 50 bar and at loadings of 0.1 to 1.5 v/vh. The palladium content of the catalyst preferably ranges from 2.2 to 4% by weight.

Surprisingly, it was found that the effectiveness of the dechlorination is high only if the starting catalyst is free of chlorine, although the catalyst becomes chlorine-containing during the catalytic reaction. The cause of this is suspected to lie in the fact that a metal crystallite size distribution, which is optimum for the hydrodechlorination, is obtained only in the chlorine-free state of the starting catalyst.

The distribution of the palladium over the cross section of the support is essential for the inventive use. Surprisingly, it was found that the hydrodechlorination conversion is highest, when the palladium concentration over the cross section of the hydrodechlorination catalyst support used passes through a maximum in the region from 50 to 250 μm below the outer surface of the support. In this region, the palladium concentration is 1.5 to 7 times the average concentration of the catalyst. As catalyst supports, strands of different shape, such as solid strands, hollow strands, strands with a clover profile, etc., and sphere or pills can be used. The diameter of the supports advisably should fall within the range of 1 to 4 mm.

The high activity of the catalyst permits the hydrodechlorination of chlorinated hydrocarbons to be carried out at temperatures below 230° C. with a degree of conversion of at least 99.98% over a period of at least 2,500 hours without having to regenerate the catalyst. Residual gas, resulting from prior absorption of the hydrogen chloride, is directly supplied for thermal utilization without requiring further purification or removal of hydrocarbon and hydrogen chloride adsorptively and absorptively from the residual gas.

As chlorinated hydrocarbons, chlorinated alkanes, chlorinated alkenes or chlorinated aromatic compounds, for example, can be used. Most advisably, the reaction is carried out in a straight passage. Because of the high heat of reaction, the catalyst is most advisably disposed in tubular reactors. The mixture of chlorinated hydrocarbon and hydrogen can be passed through the catalyst layer with a carrier gas, such as nitrogen or methane, or without a carrier gas.

The economic and thermal usability of the reaction products are special advantages of the inventive use.

The hydrogen chloride, formed by the hydrodechlorination, is absorbed in water. Because of the high degree of conversion of the hydrodechlorination, the quality of the resulting hydrochloric acid complies with the DIN regulations.

The $C_1$ to $C_3$ hydrocarbons formed, together with the residual hydrogen, advisably are utilized thermally after the adsorption of the hydrochloric acid. Higher hydrocarbons can be separated before the absorption of hydrogen chloride and utilized as such. For this application, a cycling method is particularly suitable.

EXAMPLE I

A palladium-containing catalyst is prepared as follows. Amorphous aluminosilicate, in the form of 1.8 mm strands with a surface area of 342 m$^2$/g and a silica content of 35% by weight is saturated with a palladium nitrate solution up to its water absorption capacity. The support, prepared in this way, is dried for 3 hours at 110° C. and tempered in air for 2 hours at 450° C. The catalyst contains 4.1% by weight of palladium. The palladium concentration over the cross section of the catalyst support is a maximum at 120 to 160 μm below the outer surface and has values there of 10 to 16% by weight.

The catalyst (500 mL) is transferred to a reaction tube, which is 1 m long and has an internal diameter of 3.9 cm, heated in a stream of hydrogen (150 L/h) to 300° C. and left for 3 hours at this temperature. Subsequently, the catalyst is cooled to 175° C. and charged with a mixture of hydrogen and 1,2-dichloropropane at atmospheric pressure, the catalyst loading being 0.14 L/h and the molar ration of 1,2-dichloropropane to hydrogen being 1:4. The quantitative composition of the reaction product was determined by means of GC-MS. The analyses revealed that the catalyst still converted 1,2-dichloropropane 100% after 2500 hours of use.

EXAMPLE 2

The procedure of Example 1 is followed; however, the catalyst contains 42% by weight of silica and 3.2% by weight of palladium, the concentration of palladium over the cross section of the catalyst casting being a maximum at 70 to 110 μm below the outer surface. The palladium concentration at the maximum is 6.5 to 9.8% by weight. Analyses revealed that, after 2,500 hours, the catalyst still converted 1,2-dichloropropane completely to propane and HCl.

EXAMPLE 3

The catalyst (500 mL), described in Example 1, is transmitted to the reactor described there, heated to 280° C. in a stream of hydrogen (150 L/h) and kept at this temperature for 3.5 hours. Subsequently, the catalyst is cooled under a stream of hydrogen to the reaction temperature of 68° C. At this temperature, a mixture of trichlorobenzene, nitrogen and hydrogen is passed over the catalyst at atmospheric pressure at a loading of 0.2 L of trichlorobenzene/Lh and a molar ratio of trichlorobenzene to nitrogen plus hydrogen of 1: 48. The molar ratio of hydrogen to nitrogen was 1:8. By means of this reaction, trichlorobenzene (a mixture of 86% 1,2,3-trichlorobenzene, 11.2% 1,3,5-trichlorobenzene and 2.5% 1,2,4-trichlorobenzene) was converted completely to cyclohexane and HCl. After 2,500 hours, no loss in activity was detected.

EXAMPLE 4

(Comparison Example)

γ-Alumina, in the form of strands with diameters of 1.7 to 1.9 mm, is saturated with an aqueous solution of rhodium (III) chlorhydrate. The support, treated in this way, is dried in air at 110° C. and subsequently reduced for 2 hours in a stream of hydrogen at 250° C. The catalyst contains 1% by weight of rhodium. This catalyst was tested under the conditions of Example 1. After a reaction time of only 670 h, already 90 ppm of dichloropropane were detected at the reactor outlet.

EXAMPLE 5

A catalyst (100 mL) with the following properties is transferred to a tubular reactor:

| | |
|---|---|
| Composition: | 2.4% by weight of palladium on an $Al_2O_3$-$SiO_2$ support containing 40% by weight of $SiO_2$ |
| Pd Distribution: | The maximum palladium concentration is 4.9 to 6.4% by weight and is encountered about 60 to 80 μm below the outer surface of the support. |
| Shape: | Solid strands with a diameter of 1.8 mm |
| BET Surface Area: | 326 m$^2$/g |
| The tubular reactor has a length of 60 cm and a diameter of 1.6 cm. | |

For activation, the catalyst is heated in a stream of hydrogen (30 L/h) under atmospheric pressure at 5°

C./minute to 300° C. and treated at this temperature for 4 hours. After that, the catalyst is cooled to 170° C. in a stream of hydrogen and charged at this temperature with a mixture of 10 mL of 1,2-dichloropropane/h and 8 L of hydrogen/h at a pressure of 3.5 bar and a temperature of 215° C. A temperature profile with a maximum temperature of 225° C. developed in the catalyst filling. The 1,2-dichloropropane is converted completely to propane and hydrogen chloride.

After the catalyst has been used for 2,500 hours, the reaction still proceeds to completion, that is, the catalyst shows no loss of activity.

EXAMPLE 6

A catalyst with the following characteristics is incorporated in the tubular reactor:

| | |
|---|---|
| Composition: | 2.9% by weight of palladium on an $Al_2O_3$-$SiO_2$ support containing 45% by weight of $SiO_2$ |
| Pd Distribution: | The maximum palladium concentration is 6.9 to 12.3% by weight and is encountered about 55 to 105 μm below the outer surface of the support. |
| Shape: | Spheres with a diameter of 1.9 to 2.3 mm |
| BET Surface Area: | 291 m$^2$/g |

The tubular reactor has the same dimensions as the one used in Example 5.

For activation, the catalyst is heated in a stream of hydrogen (30 L/h) under atmospheric pressure at a rate of 3° C./min to 340° C. and left at this temperature for 3 hours under flowing hydrogen. After the catalyst has cooled to 165° C., a mixture of 22 mL of 1,2-dichloropropane/h and 18 L of hydrogen/h are passed through the catalyst filling at a pressure of 4.5 bar. An axial temperature profile develops in the catalyst layer with a maximum temperature of 218° C. There is complete conversion of the 1,2-dichloropropane to propane and hydrogen chloride, which is removed from the reaction product by absorption in water.

Even after a reaction time of 2,500 hours, the conversion by the catalyst used is still complete.

EXAMPLE 7

The catalyst (100 mL), described in Example 5, is activated in the same tubular reactor under analogous conditions, subsequently cooled to 140° C. and charged at this temperature with a mixture of 12 mL of 1,2,4-trichlorobenzene/h and 15 L of hydrogen/h at atmospheric pressure. 1,2,4-trichlorobenzene is converted completely to cyclohexane and hydrogen chloride. Even after a reaction time of 2,600 hours, the catalyst still converts the trichlorobenzene completely.

EXAMPLE 8

A catalyst (100 mL) with the following characteristics is incorporated into the reactor of Example 5:

| | |
|---|---|
| Composition: | 4.0% by weight of palladium on an $Al_2O_3$-$SiO_2$ containing 40% by weight of $SiO_2$ |
| Pd Distribution: | The maximum palladium concentration is 11.8 to 18.4% by weight and is encountered about 60 to 110 μm below the outer surface of the support. |
| Shape: | Spheres with a diameter of 1.5 to 2 mm |
| BET Surface Area: | 328 m$^2$/g |

To activate it, the catalyst is heated in a stream of hydrogen (20/L) at atmospheric pressure at a rate of 3° C./min to 310° C. and kept at this temperature for 3 hours. After the catalyst has cooled to 72° C., a mixture of 10 mL 1,2,4-trichlorobenzene/h and 30 L of hydrogen/h are passed through the catalyst fill. The chlorinated hydrocarbon is converted completely to cyclohexane and hydrogen chloride over a period of 2,500 hours.

We claim:

1. A hydrodehalogenation catalyst for the hydrogenating disposal of halogenated hydrocarbons comprising a support of aluminosilicate saturated with a chlorine-free palladium salt solution, the palladium being present in an amount of 0.5 to 8% by weight and silica being present in an amount of 1 to 50% by weight, the palladium concentration over a cross section of the support passing through a maximum of 50 to 250 μm below an outer surface of the support and being 1.5 to 7 times an average palladium concentration of the catalyst, and the catalyst being prepared by impregnating the support with a chlorine-free palladium salt solution, the ratio of solution volume to support volume being at most 2:1, drying the catalyst and reducing the catalyst in a stream of hydrogen at temperatures between 100° and 500° C.

2. The hydrodehalogenation catalyst of claim 1, wherein the palladium content is 2.2 to 6% by weight and the silica content is 35 to 45% by weight.

3. The hydrodehalogenation catalyst of claim 1, wherein the chlorine-free palladium salt solution is a palladium nitrate solution.

4. The hydrodehalogenation catalyst of claim 1, wherein the preparation of the catalyst further comprises the step of calcining the catalyst at 350° to 450° C. prior to the step of reducing the catalyst.

5. A hydrodehalogenation catalyst comprising a support of aluminosilicate saturated with a chlorine-free palladium salt solution, the palladium being present in an amount of 0.5 to 8% by weight and the silica being present in an amount of 1 to 50% by weight, the palladium concentration over a cross section of the support passing through a maximum of 50 to 250 μm below an outer surface of the support and being 1.5 to 7 times an average palladium concentration of the catalyst.

6. A method of using the hydrodehalogenation catalyst of claim 5 for the catalytic hydrodehalogenation of halogenated hydrocarbons or of industrial mixtures containing halogenated hydrocarbons comprising contacting halogenated hydrocarbons or industrial mixtures containing halogenated hydrocarbons with the catalyst at temperatures of 30° to 350° C. and at a pressure of up to 50 bar.

7. The use method of claim 6, wherein the palladium content of the catalyst is 2.2 to 4% by weight.

8. The method of claim 3, wherein conversion of the chlorinated hydrocarbons is at least 99.98% over a period of at least 2,500 hours without regenerating the catalyst and residual gas, resulting film prior absorption of the hydrogen chloride, is directly supplied to thermal utilization.

9. The method of using the hydrodehalogenation catalyst of claim 6, wherein the catalyst is loaded at a rate of 0.1 to 1.5v/vh.

10. The method of using the hydrodehalogenation catalyst of claim 6, wherein the catalyst contacts chlorinated hydrocarbons or industrial mixtures containing chlorinated hydrocarbons.

11. The hydrodehalogenation catalyst of claim 5, wherein the chlorine-free palladium salt solution is a palladium nitrate solution.

12. A method of making a hydrodehalogenation catalyst comprising impregnating an aluminosilicate support with a chlorine-free palladium salt solution to produce a catalyst, the ratio of solution volume to support volume being at most 2:1, drying the catalyst and reducing the catalyst in a stream of hydrogen at temperatures between 100° and 500° C.

13. The method of claim 12, further comprising calcining the catalyst at 350° to 450° C. prior to reducing the catalyst.

* * * * *